(12) United States Patent
Barker et al.

(10) Patent No.: US 7,029,163 B2
(45) Date of Patent: Apr. 18, 2006

(54) APPARATUS FOR MIXING AND DISPENSING COMPONENTS

(75) Inventors: Donald Barker, Sandy Hook, CT (US); Roy B. Bogert, Lincoln Park, NJ (US); John P. Carr, River Vale, NJ (US); James W. Nelson, Morristown, NJ (US); Linda M. Trebing, Madison, NJ (US); Kenneth R Gleason, Woodbridge, CT (US); Damian Bianchi, Durham, CT (US)

(73) Assignee: Advanced Biomaterial Systems, Inc., Chatham, NJ (US)

( * ) Notice: Subject to any disclaimer, the term of this patent is extended or adjusted under 35 U.S.C. 154(b) by 42 days.

(21) Appl. No.: 10/637,908

(22) Filed: Aug. 8, 2003

(65) Prior Publication Data

US 2004/0196735 A1  Oct. 7, 2004

Related U.S. Application Data

(63) Continuation-in-part of application No. 10/438,471, filed on May 15, 2003, and a continuation-in-part of application No. 10/266,053, filed on Oct. 7, 2002, now Pat. No. 6,572,256, and a continuation-in-part of application No. 10/417,553, filed on Apr. 17, 2002, now abandoned.

(60) Provisional application No. 60/424,398, filed on Nov. 6, 2002.

(51) Int. Cl.
*B01F 7/14* (2006.01)
*B01F 13/06* (2006.01)
*B01F 15/02* (2006.01)

(52) U.S. Cl. ............... 366/139; 366/184; 366/192; 366/195

(58) Field of Classification Search .......... 366/130, 366/139, 189, 192, 194, 195, 154.1, 155.1, 366/182.1, 182.3, 182.4, 131, 184, 196; 222/236, 222/239, 241; 604/131, 93.01
See application file for complete search history.

(56) References Cited

U.S. PATENT DOCUMENTS

| | | | | |
|---|---|---|---|---|
| 5,265,956 A | * | 11/1993 | Nelson et al. | ........... 366/139 |
| 5,344,232 A | * | 9/1994 | Nelson et al. | ........... 366/139 |
| 5,368,386 A | * | 11/1994 | Murray | ........... 366/139 |
| 5,876,116 A | * | 3/1999 | Barker et al. | ........... 366/182.3 |
| 5,961,211 A | * | 10/1999 | Barker et al. | ........... 366/182.3 |

(Continued)

FOREIGN PATENT DOCUMENTS

DE  201 18 004 U 1  11/2001

Primary Examiner—Tony G. Soohoo
(74) Attorney, Agent, or Firm—Fish & Richardson P.C.

(57) ABSTRACT

Apparatus and methods for mixing and dispensing components. The methods and apparatus of the invention are particularly advantageous to manually mix the components of radiopaque bone cement and inject the resulting radiopaque bone cement into skeletal structures. The manually actuated apparatus of the invention comprises: (1) a sealed mixing chamber for mixing components; (2) a dispensing chamber isolated from the sealed mixing chamber; (3) a controllable portal to open a flow path between the sealed mixing chamber and the dispensing chamber so that the dispensing chamber can receive the mixed components after they are mixed; and (4) a drive mechanism associated with the dispensing chamber to force the mixed contents from the dispensing chamber.

13 Claims, 15 Drawing Sheets

U.S. PATENT DOCUMENTS

| | | | |
|---|---|---|---|
| 6,024,480 A * | 2/2000 | Seaton et al. | 366/130 |
| 6,033,105 A | 3/2000 | Barker et al. | 366/139 |
| 6,116,773 A * | 9/2000 | Murray | 366/139 |
| 6,572,256 B1 * | 6/2003 | Seaton et al. | 366/139 |
| 2002/0013553 A1 | 1/2002 | Pajunk et al. | 604/187 |
| 2004/0066706 A1 * | 4/2004 | Barker et al. | 366/139 |

* cited by examiner

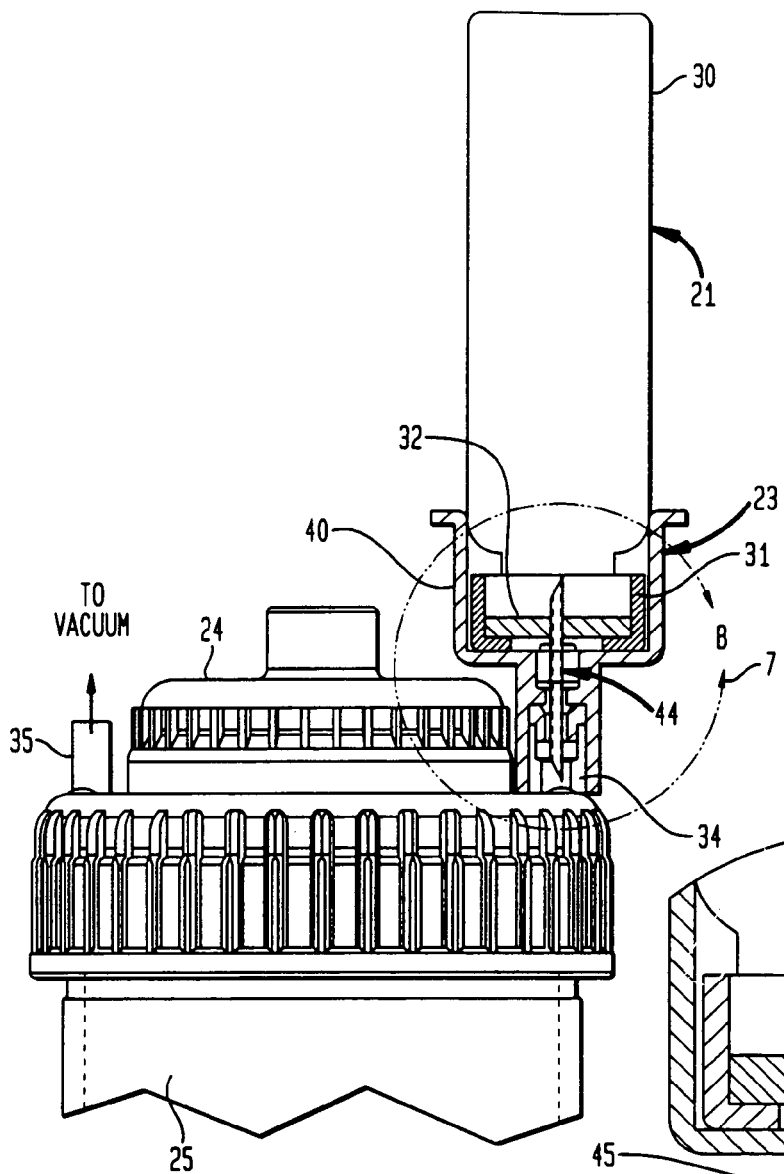
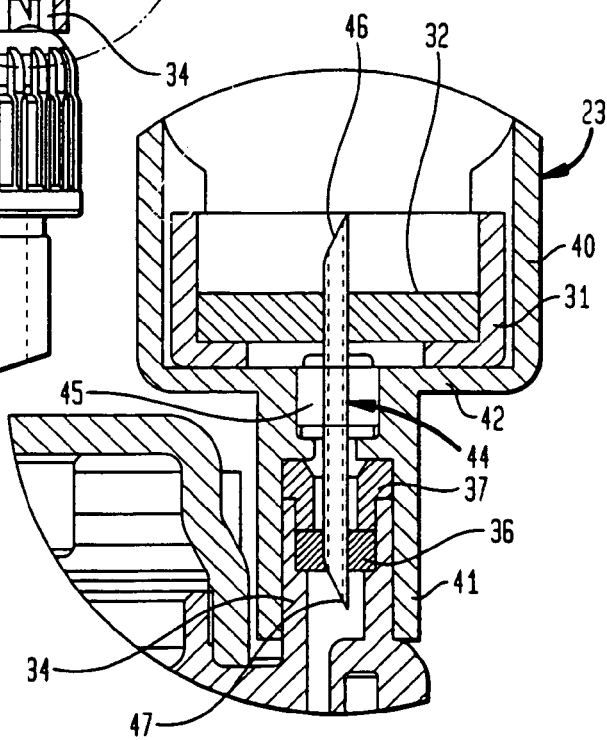
FIG. 6
FIG. 7

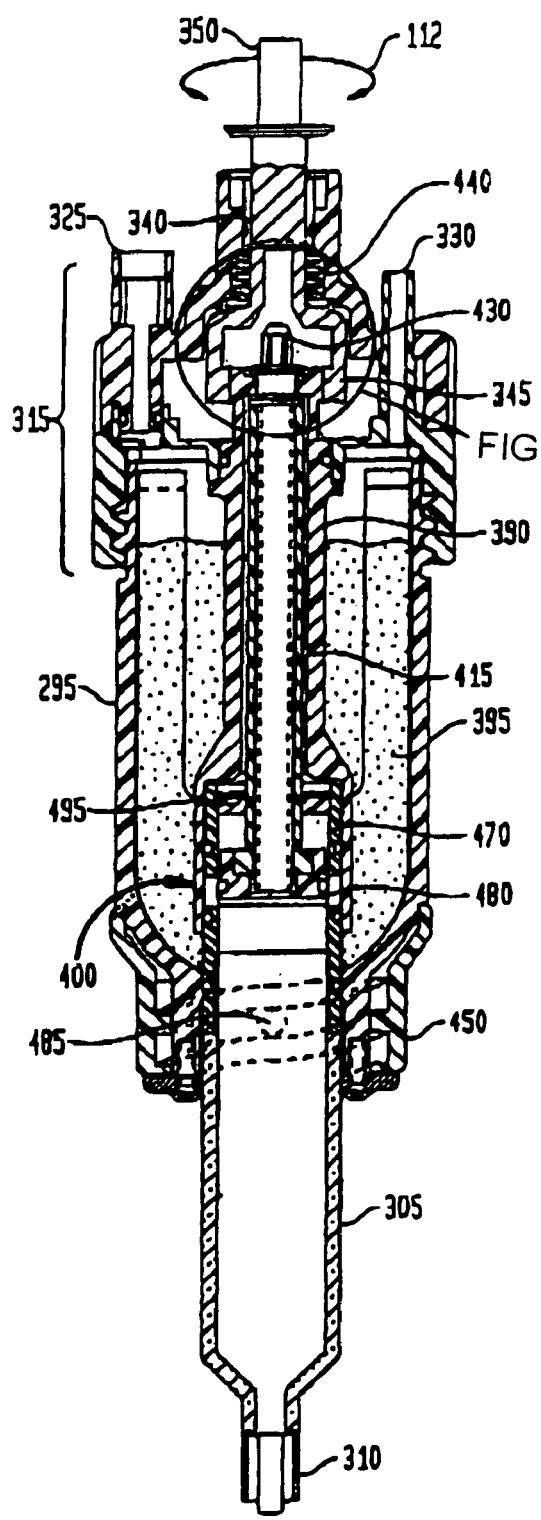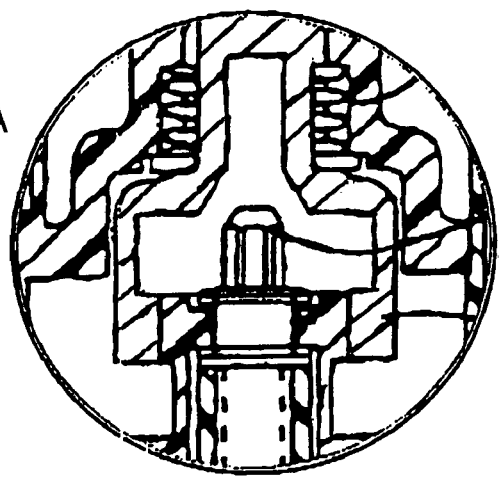
FIG. 15A
FIG. 15

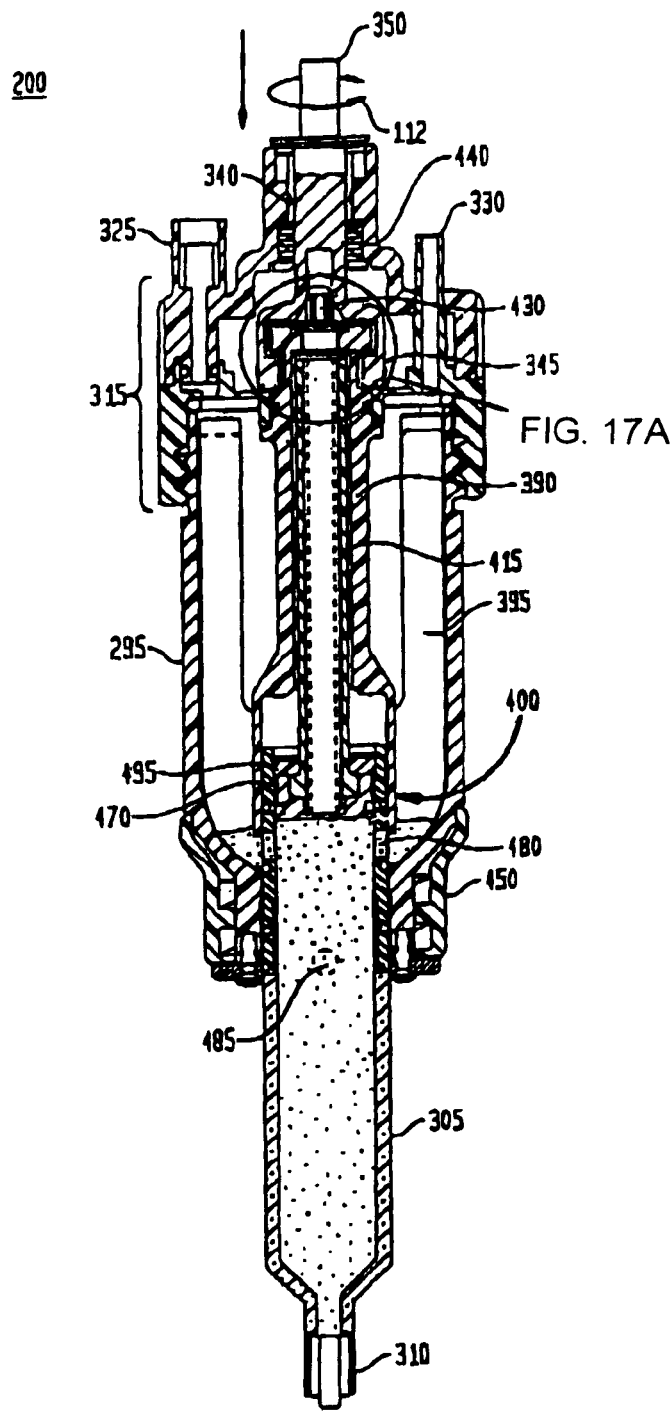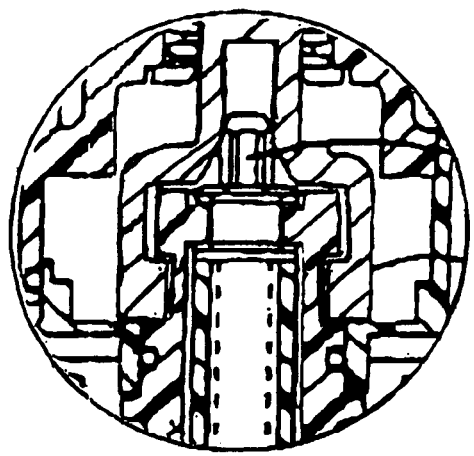
FIG. 17A
FIG. 17

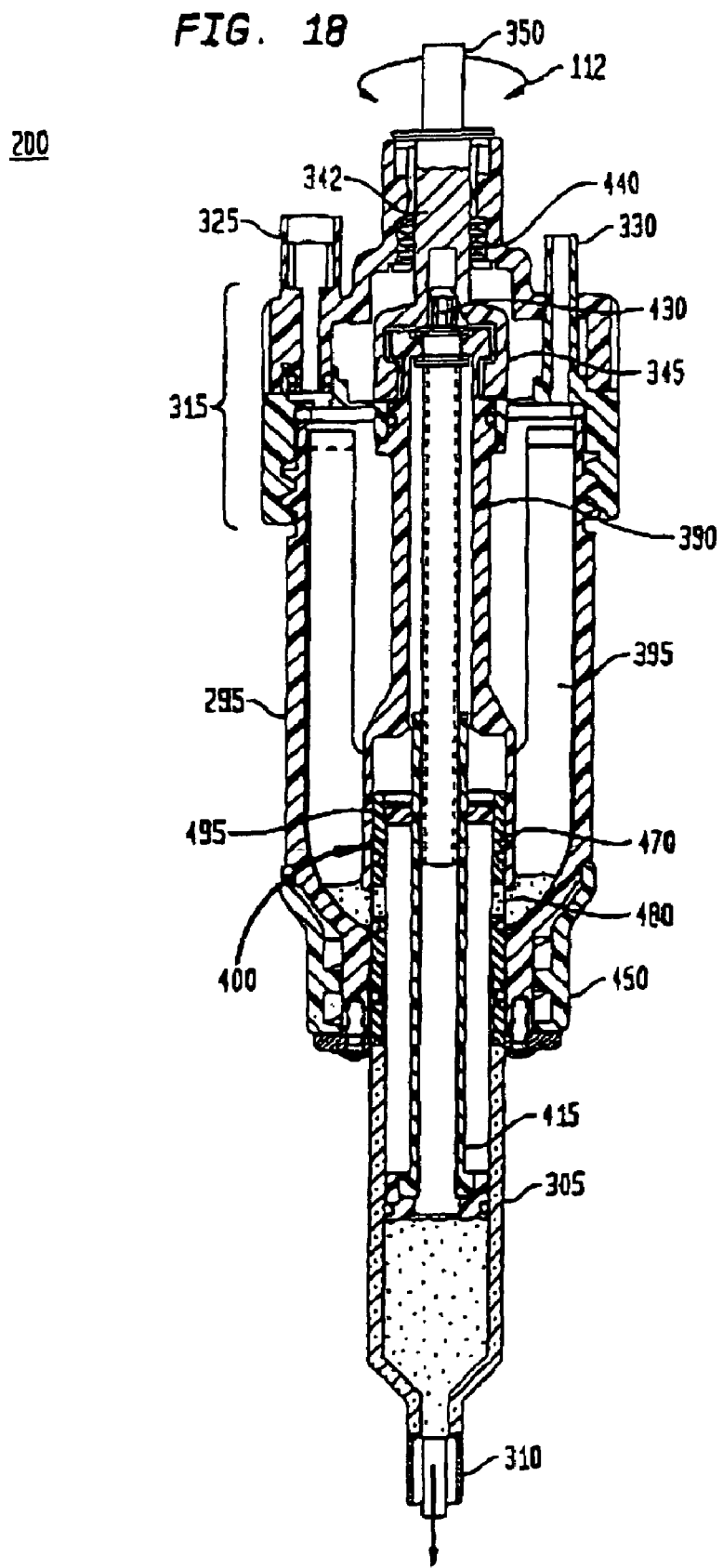

APPARATUS FOR MIXING AND DISPENSING COMPONENTS

1. CROSS REFERENCE TO RELATED APPLICATIONS

This application is a continuation-in-part of U.S. patent application Ser. No. 10/438,471 filed by D. Barker et al. on May 15, 2003, and entitled "Apparatus For Mixing And Dispensing Components". The parent Ser. No. 10/438,471 application is incorporated herein by reference.

The parent application is also a continuation-in-part of application Ser. No. 10/266,053, now U.S. Pat. No. 6,572,256, filed on Oct. 7, 2002, entitled "Multi-component, Product Handling And Delivery System", by J. Seaton et al., which application is hereby incorporated herein by reference.

This application is a continuation-in-part of application Ser. No. 10/417,553, now abandoned, filed on Apr. 17, 2003, entitled "Multi-component Handling And Delivery System", by J. Seaton et al., which application is hereby incorporated herein by reference.

This application also claims the benefit of U.S. Provisional Application No. 60/424,398 filed on Nov. 6, 2002, entitled "Multi-component, Product Handling And Delivering System For Bone Void And Fracture Filling", by L. Trebing et al. , which application is hereby incorporated herein by reference.

2. FIELD

This invention relates to methods and apparatus for mixing and dispensing at least two components. The apparatus and methods of the invention are particularly useful to prepare bone cement and deliver the bone cement into the skeletal structure of patients, such as to injured spinal vertebrae.

3. BACKGROUND

Numerous spinal vertebrae fractures occur each year, many in older women as a result of osteoporosis. The pain and loss of movement accompanying vertebral fractures severely limits activity and reduces the quality of life. In contrast to typical bone fractures, the use of surgery to treat vertebral fractures is extremely difficult and risky. A procedure called "vertebroplasty" is a less-invasive alternative to surgery, with fewer attendant risks, and has proved extremely effective in reducing or eliminating the pain caused by spinal fractures.

Vertebroplasty involves injecting radiopaque bone cement into the damaged vertebral body by way of a needle or cannula using x-ray (fluoroscopy) to visualize and monitor delivery. Generally, vertebroplasty is performed by radiologists, neurosurgeons, and orthopedic surgeons.

Directly prior to injection, bone cement is prepared by mixing bone-cement powder (e.g., polymethylmethacrylate "PMMA"), liquid monomer (e.g., methyl methacrylate monomer), with an x-ray contrast agent (e.g., barium sulfate), to form a fluid mixture. The components of bone cement must be kept separate from each other until the user is ready to mix them to form the desired bone cement. Typically, bone-cement powder is stored in a flexible bag, pouch, bottle, or similar container, while the liquid monomer is stored for shipment and handling in a vial or tube, usually formed from glass. Bone cement sets and hardens rapidly, so the doctors must work quickly and efficiently. A typical bone-cement mixture may comprise 15 g polymethylmethacrylate powder, 5–10 g of methyl methacrylate monomer, and 5–8 grams of sterile barium sulfate for radiographic visualization of the cement. The radiopaque bone-cement mixture is placed in a cannula-type dispensation system, the needle portion is inserted into the patient, properly positioned, and the bone cement slowly injected into the subject vertebra using x-ray guidance allowing the doctors to see the mixture actively infuse. When enough of the cement is injected into the damaged bone, as seen by x-ray, the flow is stopped and the needle is removed. However, as discussed below, stopping the flow is easier said than done. There are serious control problems with current cannula-type bone-cement dispensation systems.

While the procedure itself has proven very effective, problems are associated with handling and mixing the bone cement. Bone cement hardens very quickly, even more so upon exposure to air. Also, it is important that the cement delivered into the bone be virtually free of any entrapped air bubbles or air pockets. In spite of this, bone cement is typically hand mixed in an open environment directly before the procedure using a tongue depressor or spatula. The mixed cement is then manually transferred from the mixing vessel to a separate dispensing device, such as a syringe. Removal of the mixed cement from the mixing vessel into the caulking gun or syringe is cumbersome, time consuming, and has the potential for being mishandled, dropped or contaminated. In any case, the resulting bone cement, since it has been exposed to air, is less fluid and harder to force through the cannula into the vertebrae. Accordingly, more pressure must be exerted by the attending physician on the dispensing device. The increased pressure requirement makes control difficult and increases the likelihood that too much cement will be injected. For example, when the x-ray indicates that the vertebrae is filled, it is difficult to stop the cement flow out of the cannula and overflow of the cement into the surrounding tissues can result. This is unsafe for the patient since the excess cement may leak out of the vertebral body into surrounding tissue and vascular structures. In some cases, surgery may be required to remove the excess cement.

Another disadvantage with current bone cement mixing protocols that require open-air transfers stems from the toxic nature of the liquid monomer component. Bone cement monomers, including methyl methacrylate, give off toxic vapor and are irritating to the eyes and respiratory system. Furthermore, acrylate monomer irritates skin and contact with minute concentrations can cause sensitization. Accordingly, handling requires the use of suitable gloves. So, not only must attending clinicians worry about the deleterious effects of incorporating air bubbles into the bone cement during the cumbersome hand mixing, but also be concerned with health and safety issues in connection with toxic methyl methacrylate vapors.

Currently, many clinicians begin the bone-cement mixing process by first opening a glass vial containing the liquid monomer component. One common method for opening glass vials is to snap off the top of the vial at the smallest cross section. Unfortunately, this method risks injury to operating-room personnel from broken glass or sharp edges. Another disadvantage is that small glass shards often form during such breaking, which can fall into the cement mixture. In attempting to expedite the opening of the vial or tube holding the liquid monomer, as well as reduce any exposure to the foul odor possessed by the liquid monomer, various prior art systems have been developed for enabling the user to insert the sealed vial or tube into an area of the vessel and then break the vial or tube for releasing the liquid monomer directly into the dry powder.

These prior art systems all require that the broken glass pieces or shards of the vial/tube must be separately retained and prevented from reaching the bone cement product. In attempting to satisfy this requirement, substantial construction and operational difficulties have occurred with these prior art systems. Furthermore, in other prior art systems, manual addition of the monomer is required, exposing the user to the foul odor of the monomer and the substantial difficulties typically encountered in handling such products.

What is needed is a mixing and dispensing device that can mix the components of bone cement in a sealed environment and provide increased control on dispensation so that the operator can readily stop the bone-cement flow when the desired amount has been dispensed.

4. SUMMARY

The invention relates to apparatus, kits, and methods for mixing and dispensing components. The methods and apparatus of the invention can be adapted to mix and dispense any components but are particularly useful where the components require isolation from the surrounding atmosphere, for example, in cases where the components are adversely affected by air or because the components give off toxic vapors. The methods and apparatus of the invention are particularly appropriate where controlled and consistent mixing and dispensing are desired as well as limiting the exposure of those in proximity to any noxious fumes generated during the mixing process.

In one embodiment, the invention is directed to a mixing and dispensing unit for mixing and dispensing biocompatible bone fillers. The mixing and dispensing unit of the invention is useful to mix and dispense the components of biocompatible bone fillers for delivery into human or animal patients. Examples of biocompatible fillers suitable for use in the invention include, but are not limited to, bone cements, calcium-based fillers, bioglass, bone substitutes, and grafts. In addition, the mixing and dispensing unit of the invention allows facile addition of other components before or during the mixing process, for example, antibiotics, colorants, bone-morphogenic proteins, and opacifying agents.

The mixing and dispensing unit of the invention is useful in many medical procedures involving the preparation and delivery of biocompatible bone fillers into patients (both humans and animals), for example, vertebroplasty, tumor or bone-void filling, dental applications, in the treatment of a vascular necrosis, and many others.

The mixing and dispensing unit of the invention is particularly suited to mix the components of radiopaque PMMA-based bone cement and inject the resulting radiopaque bone cement to repair, reinforce, or replace injured, diseased, or insufficient bone or skeletal structures, such as to injured or diseased spinal vertebrae of human or animal patients. Preferably, delivery is accomplished by way of a tube, hose, cannula, or needle.

The apparatus of the invention for mixing and dispensing components comprises: (1) a sealed mixing chamber for mixing components; (2) a dispensing chamber isolated from the sealed mixing chamber; (3) a controllable portal to open a flow path between the sealed mixing chamber and the dispensing chamber so that the dispensing chamber can receive the mixed components after they are mixed; and (4) a drive mechanism associated with the dispensing chamber to force the mixed contents from the dispensing chamber.

The sealed mixing chamber comprises a mixing unit; an access portal for receiving the components; and a vacuum portal for attachment to a vacuum supply. The mixing and dispensing unit of the invention is preferably used in conjunction with a sealed container, which stores liquid monomer separately. In a preferred embodiment, the sealed mixing chamber is pre-packaged with bone-cement powder and the access portal is designed to sealably receive liquid monomer from the sealed container. In order to attain the desired transfer of the liquid monomer from the sealed vial or tube directly into the dry powder, without exposing the user to the liquid monomer, the mixing and dispensing unit of the invention comprises a transfer assembly, preferably, a fluid transfer assembly. The transfer assembly of the invention is constructed for cooperating with the sealed container containing the liquid monomer and the sealed mixing chamber for extracting the liquid monomer from the container in a closed loop operation and directly delivering the liquid monomer into the sealed mixing chamber containing the dry powder. This transfer operation is achieved upon demand by the user, while preventing those in the surrounding area from being exposed to the liquid monomer or noxious fumes.

The sealed mixing chamber controllably communicates with the dispensing chamber by a controllable portal. In the mixing phase, the controllable portal is closed. After mixing is complete, the controllable portal is opened creating a flow path whereby the dispensing chamber receives the bone cement. The dispensing chamber comprises a dispensing portal, preferably, adapted to connect to a flexible tube, high-pressure hose, cannula, or a standard needle to deliver the mixed bone cement to a patient's vertebra. The dispensing chamber also communicates with a drive mechanism for forcing the bone cement through the dispensing portal and into the vertebroplasty delivery tube. In preferred embodiment, a single drive connection is used to mix the components and to dispense the components thereby reducing the number of manipulations required for mixing and dispensing bone cement.

In an advantageous embodiment, the access portal of the sealed mixing chamber comprises a self-sealing elastic member to permit injection of the liquid component via a needle. In a preferred embodiment, The mixing unit comprises a helical mixing vane, and the drive mechanism for delivery is a reversible plunger. The apparatus can include a mechanical switch for changing the configuration of the apparatus from a component mixing state to a mixture dispensing state.

A preferred exemplary embodiment is manually actuable to mix and dispense liquid and powder components for bone cement without power tools or power outlets.

5. BRIEF DESCRIPTION OF THE FIGURES

These and other features, aspects, and advantages of the present invention will become better understood with regard to the following description, examples, appended claims, and accompanying drawings where:

FIG. 6 is a side elevation view of the fully assembled multi-component system of the present invention, partially broken away and partially in cross-section;

FIG. 7 is an enlarged cross-sectional side elevation view detailing area 7 of FIG. 6;

FIG. 15 is a cross-sectional view of a mixing and dispensing unit of the invention in the mixing stage;

FIG. 15A is an enlarged view of part of FIG. 15.

FIGS. 17 and 18 are cross-sectional views of a mixing and dispensing unit of the invention depicting the mixed components being dispensed from the dispensing chamber.

FIG. 17A is an enlarged view of part of FIG. 17.

6. DETAILED DESCRIPTION

Figure 1:
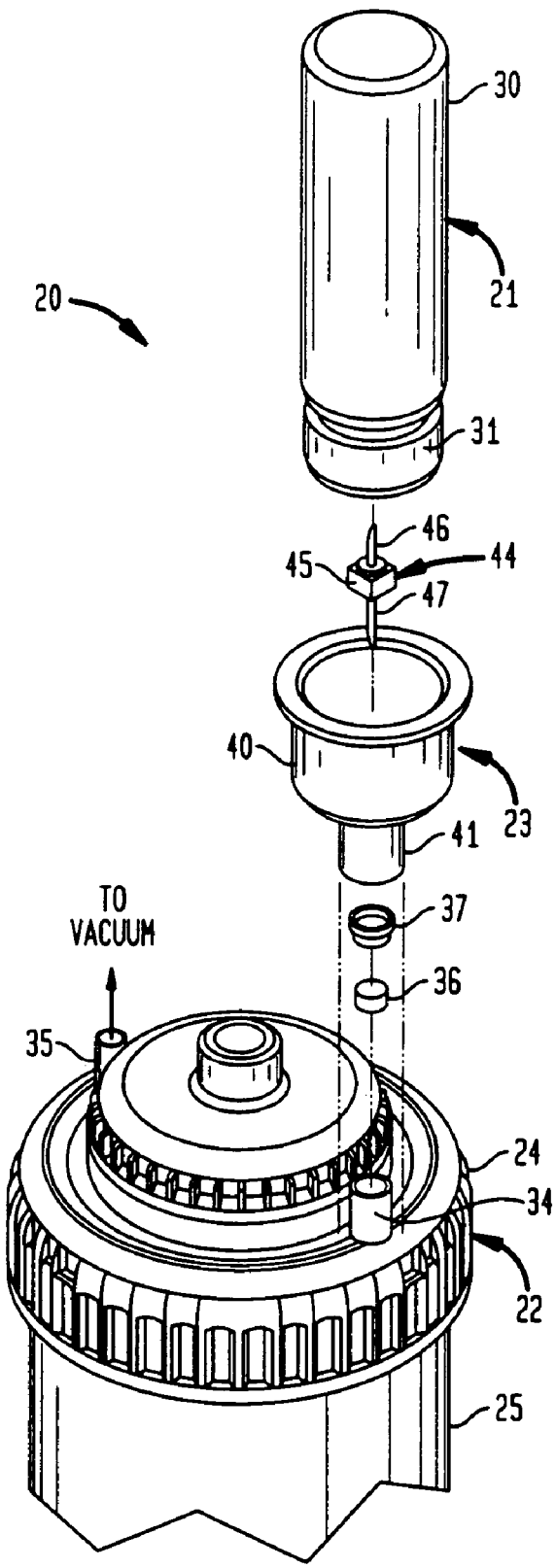
FIG. 1 is an exploded perspective view, partially broken away, depicting the multi-component product handling and delivering system of the present invention.

By referring to FIGS. 1–11, along with the following detailed discussion, the construction and operation of the preferred multi-component product handling and delivering systems of the present invention can best be understood. However, as will become evident from this disclosure, further alternate embodiments of the present invention can be implemented without departing from the scope of the present invention. Consequently, the embodiments detailed in FIGS. 1–11, and in the following detailed disclosure, are intended for exemplary purposes, and not as a limitation of the present invention.

The present invention can be employed with any type of vessel used to intermix the two or more components. Thus, the present invention is not limited to combining or mixing bone cements.

The components of the multi-component product handling and delivering systems of the present invention can be packaged and sold together as a kit.

In FIGS. 1, 2, 6, and 7, multi-component product handling and delivering system 20 of the present invention is fully depicted as comprising container 21, integrated bone cement handling and delivery system 22, and transfer assembly 23, preferably, a fluid transfer assembly. Container 21 is preferably a sealed container, more preferably, a sealed container designed for containing corrosive chemicals, such as liquid monomer. As used herein, "sealed" means that the container's contents are prevented from leaking during handling and transport and are protected from air. As shown, integrated bone cement handling and delivery system 22 comprises cover 24 that is threadedly mounted to vessel 25.

Figure 2:
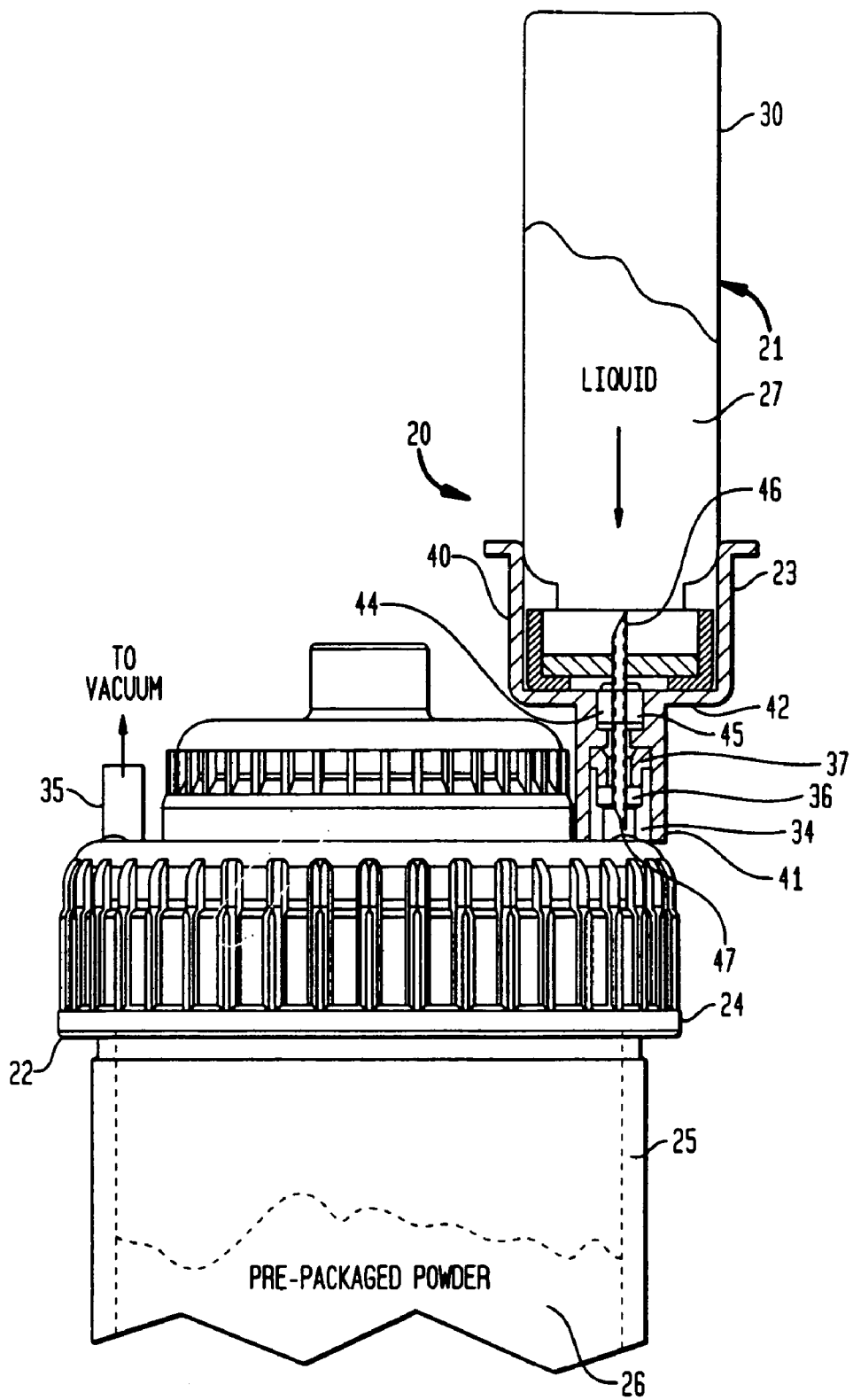
FIG. 2 is a side elevation view, partially broken away and partially in cross-section depicting the multi-component product handling and delivering system of FIG. 1 fully assembled.
Figure 3:
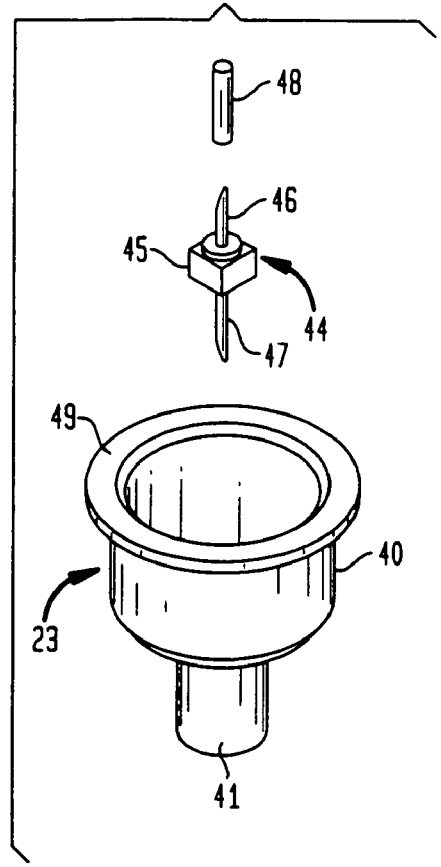
FIG. 3 is an exploded perspective view of the transfer assembly member of the multi-component product handling and delivering system of present invention.
Figure 4:
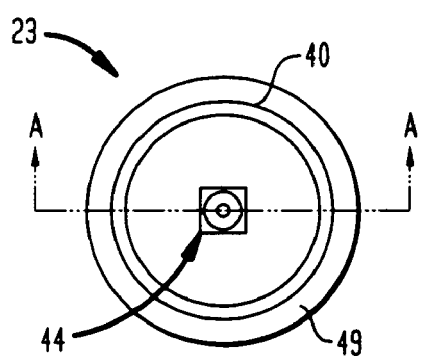
FIG. 4 is a top plan view of the transfer assembly of FIG. 3.
Figure 5:
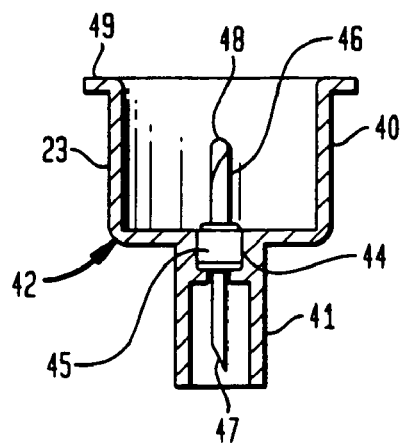
FIG. 5 is a cross-sectional side elevation view of the transfer assembly taken along the line A—A of FIG. 4.

In the preferred construction and implementation of the present invention, the second component of the bone cement, which comprises dry powder 26, is stored in vessel 25 of bone cement handling and delivery system 22, as clearly shown in FIG. 2. However, if desired, dry powder 26 may be stored in any suitable container, bag, or pouch that is opened just prior to use with the powder being added to vessel 25.

In addition to preferably shipping dry powder 26 in vessel 25 of bone cement handling and delivery system 22, the first component, which comprises liquid monomer 27, is contained in sealed container 21. Sealed container 21 can be any suitable container adaptable to create a flow path to the vessel by way of transfer assembly 23. For example, sealed container 21 can be flexible or non-flexible plastic or polymer, preferably, glass or other chemically resistant material. In one preferred embodiment, sealed container 21 comprises glass vial or tube 30 having a single opening or portal on which cap or closure 31 is mounted.

As detailed above, cap or closure 31 of sealed container 21 comprises an integrally formed sealing membrane, preferably, a septum to provide access to the interior of glass vial/tube 30. Sealing membrane 32 comprises a generally conventional construction, formed of elastomeric material, which typically comprises elastomeric plastics, rubbers, silicones, and the like. In this way, liquid monomer 27 is sealed within glass tube/vial 30, while providing access to the interior of tube/vial 30 only upon creating a flow path, for example, by using a transfer conduit, such as a suitable syringe needle.

In certain embodiments, vacuum is used to cause the sealed-container contents to transfer into the vessel (the means for transfer). In these embodiments, the vessel will comprise vacuum portal 35 for attachment to a vacuum supply. In other embodiments, sealed container 21 can be constructed such that the system of the invention can operate without vacuum. Sealed container 21 will comprise the means to transfer the container contents into vessel 25. In these embodiments, vacuum portal 35 is not required. In one such embodiment, sealed container 21 is a chemically resistant squeeze bottle or flexible bag so that container 21's contents can be squeezed into the vessel 25. In another such embodiment, sealed container 21 is preloaded with a pressurized gas that functions to push the monomer out of container 21 upon creating a flow path by connection to transfer assembly 23. Preferably, container 21's contents (e.g., monomer) is preloaded along with the pressurized gas.

In addition, cover 24 of bone cement handling and delivery system 22 comprises a access portal 34 and vacuum portal 35 that are mounted thereto and provide access to the interior of vessel 24. Vacuum portal 35 comprises a generally conventional construction that enables a vacuum source to be connected thereto, using any suitable vacuum connection. In addition, access portal 34 comprises a sealing membrane 36, preferably, a septa-like disk mounted in access portal 34 for sealing the interior of vessel 25 from the ambient air, while also enabling access to the interior of vessel 25 to be achieved by creating a flow path, for example by employing a transfer conduit, such as a suitable needle or syringe.

Finally, holder 37 is employed for maintaining sealing membrane 36 in the precisely desired position within access portal 34. By forming holder 37 with two separate and distinct diameters, one portion of holder 37 is inserted into access portal 34, while the second, larger diameter portion thereof engages the outer terminating edge of access portal 34. In this way, sealing membrane 36 is securely maintained in the desired position within access portal 34.

The construction of transfer assembly 23 of the present invention is completed by providing for mating engagement thereof with cap 31 of sealed container 21 and access portal 34 of cover 24 of handling and delivery system 22. As fully depicted in FIGS. 1–7, in its preferred embodiment, transfer assembly 23 comprises collar portions 40 and 41, interconnected with each other along support plate 42. In addition, collar portions 40 and 41 preferably comprise generally cylindrical shapes and are coaxially aligned with each other.

In addition, collar portion 40 is constructed with an inside diameter dimensioned for co-operative, frictional engagement with cap 31 of sealed container 21. In this way, when transfer assembly 23 is mounted to sealed container 21, transfer assembly 23 is frictionally engaged securely with sealed container 21, preventing any unwanted, easy dislodgment of sealed container 21 from assembly 23.

Similarly, collar 41 comprises an inside dimension constructed for mating, co-operative, sliding engagement with access portal 34 of cover 24. In addition, by designing collar 41 with an inside dimension that is slightly greater than the outside dimension of access portal 34, secure holding engagement of transfer assembly 23 with access portal 34 is achieved whenever assembly 23 is telescopically mounted into overlying engagement with access portal 34.

In order to complete the construction of transfer assembly 23, a mechanism for providing a flow path between the vessel and the sealed container, is provided. The preferred flow path is created by a transfer conduit, such as dual ended piercing conduit 44 (double-tipped syringe needle). As depicted, transfer conduit 44 comprises a support base 45, a syringe needle forming member 46 mounted to one surface of support base 45 and a syringe needle forming member 47 mounted to the opposed surface of support base 45.

In the preferred construction, syringe needle forming members 46 and 47 comprise elongated, hollow tubes mounted to support base 45 in coaxial alignment with each other, forming a continuous, elongated flow path therebetween. In addition, each syringe needle forming member 46 and 47 comprises sharp, pointed, distal ends constructed for piercing the sealing membrane 36 (any septa-like material) for gaining access to the interior associated with the sealing membrane.

In addition, base 45 of piercing element 44 is securely mounted in transfer assembly 23, preferably affixed in support plate 42. When mounted in its secure position, syringe needle forming member 46 extends into collar portion 40, substantially centrally disposed therein. In this position, syringe needle forming member 46 is peripherally surrounded by the wall forming collar portion 40 with its sharp, distal end extending toward the opening of collar 40.

Similarly, syringe needle forming member 47 is securely positioned to be centrally disposed within collar portion 40, peripherally surrounded by the wall forming collar 41. In addition, the sharp distal end of syringe needle forming portion 47 extends towards the open end of collar 41.

By employing this construction, the telescopic axial advance of transfer assembly 23 into engagement with sealed container 21 and access portal 34 of cover 24, causes syringe needle forming portions 46 and 47 to pierce the sealing membranes 32 and 36 and establish a direct fluid transfer flow path between sealed container 21 and vessel 25. In the preferred construction, in order to eliminate any unwanted injuries, tip cover 48 is preferably mounted to syringe needle forming member 46. Since the diameter of collar portion 40 is large enough to enable a finger tip to enter its open end, the use of cover 48 prior to engagement of cover 40 onto cap 31 provides the desired protection.

In addition, in the preferred construction, collar 40 comprises radially extending flange 49 formed on its terminating end. By employing flange 49, ease of use and control of collar 40 is provided.

By referring to FIGS. 8–11, along with the following detailed discussion, the construction of an alternate, preferred embodiment of transfer assembly 23 of the present invention is provided. In this embodiment, transfer assembly 23 comprises a housing 54 that incorporates collar portions 55 and 56, interconnected to each other by support wall 57. In the preferred embodiment, collar portions 55 and 56 preferably comprise generally cylindrical shapes and are vertically aligned with each other. In addition, the central axis of each collar portion is parallel to each other and offset from each other.

As with the embodiment detailed above, collar portion 56 comprises an inside diameter constructed for mating, co-operative, sliding engagement with access portal 34 of cover 24. In addition, by designing collar portion 56 with an inside diameter that is slightly greater than the outside diameter of access portal 34, secure holding engagement of transfer assembly 23 with access portal 34 is achieved whenever assembly 23 is telescopically mounted into overlying engagement with access portal 34.

In addition, collar portion 55 comprises an inside diameter dimensioned for co-operative, frictional engagement with cap 31 of sealed container 21. In addition, in this embodiment, collar portion 55 comprises a plurality of tabs 58 mounted to the inside wall of collar portion 55 that extend radially inwardly therefrom. In addition, tabs 58 are formed on the inside wall of collar portion 55 in a vertical position that is slightly greater than the vertical height of cap 31 of sealed container 21. Finally, in the preferred construction, tabs 58 are formed about the inside wall of collar portion 55 substantially equidistant from each other, thereby being spaced apart a distance of about 120°.

By employing this construction, whenever sealed container 21 is telescopically inserted into collar portion 55 of transfer assembly 23, cap 31 of sealed container 21 is frictionally engaged with collar portion 55, securely locked in position by tabs 58 engaging the edge of cap 31 and preventing telescopic removal of sealed container 21 from collar portion 55. In this way, once sealed container 21 has been mounted in secure, locked engagement with transfer assembly 23, dislodgment or removal of sealed container 21 from collar 55 is prevented.

Figure 8:
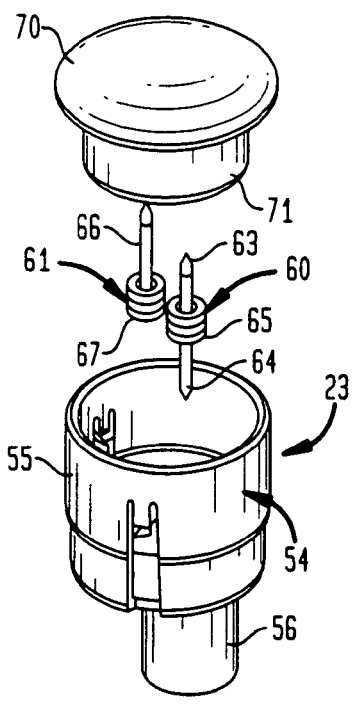
FIG. 8 is an exploded perspective view of an alternate embodiment of the transfer assembly of the present invention.
Figure 9:
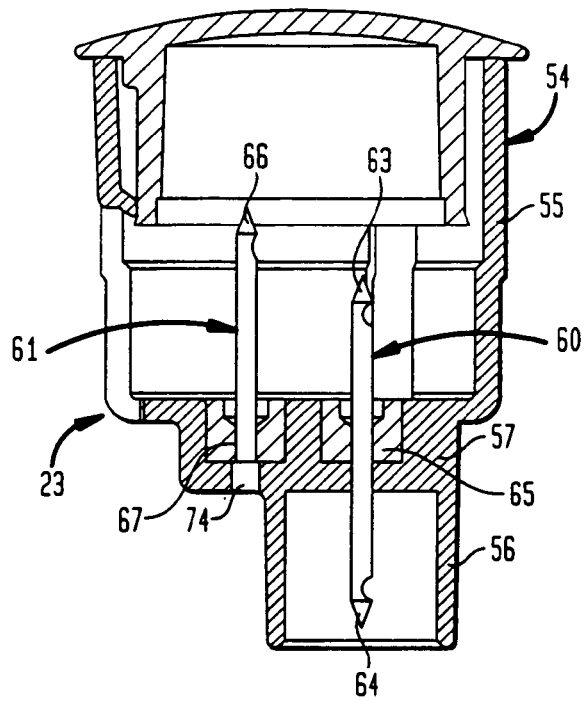
FIG. 9 is a cross-sectional side elevation view of the transfer assembly of FIG. 8.
Figure 10:
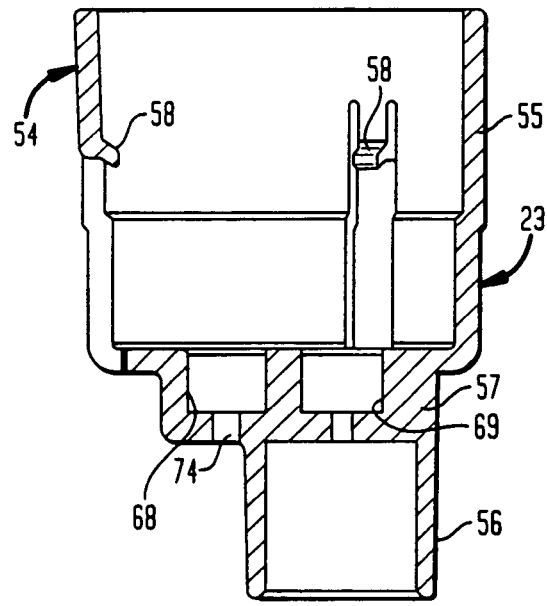
FIG. 10 is a cross-sectional side elevation view of the housing forming the transfer assembly of FIG. 8.
Figure 11:
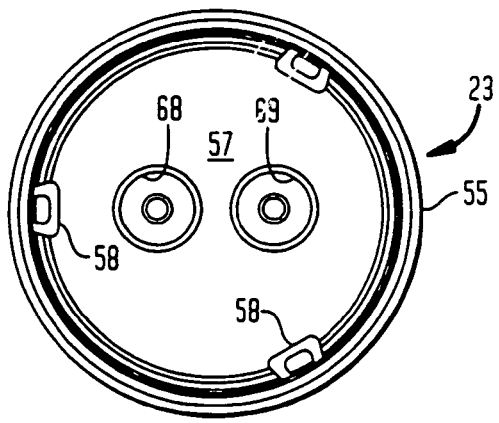
FIG. 11 is a top plan view of the housing of FIG. 10.

Furthermore, in this embodiment of the invention, transfer assembly 23 comprises gas-flow aperture 74 comprising gas-flow conduit 61 mounted in support wall 57 and transfer conduit 60 also mounted in support wall 57. Preferably, transfer conduit 60 and gas-flow conduit 61 are independent syringe needles. As shown in FIGS. 8 and 9, transfer conduit 60 comprises an elongated, continuous, tubular member that defines an elongated flow path and incorporates two separate and independent piercing ends 63 and 64 mounted to support base 65. In another embodiment, conduit 60 is molded directly into housing 54 and, thus, support base 65 is not required.

With support base 65 of transfer conduit 60 mounted in receiving hole 69 of support wall 57 of transfer assembly 23, piercing end 63 extends from support wall 57 into the interior of collar portion 55, while piercing end 64 extends from support wall 57 into collar portion 56. In this way, as detailed above, whenever transfer assembly 23 is mounted to access portal 34 of cover 24, and sealed container 21 is mounted to transfer assembly 23, the monomer contained in sealed container 21 is able to be transferred through transfer conduit 60 into vessel 25.

In this embodiment of the present invention, transfer assembly 23 also comprises a gas-flow conduit 61 that incorporates an elongated, cylindrically shaped, hollow piercing element 66 mounted to support base 67. In the preferred construction, support base 67 is mounted in receiving hole 68 formed in support wall 57 of transfer assembly 23, with hollow piercing element 66 extending therefrom into the interior of collar portion 55. In addition, base 67 of gas-flow conduit 61 cooperates with gas-flow aperture 74 formed in support wall 57, thereby providing an air flow path from the ambient surroundings through hollow gas-flow conduit 61 into the interior of sealed container 21 whenever sealed container 21 is mounted in collar 55.

By employing this embodiment of the present invention, transfer assembly 23 provides assurance that the monomer stored in sealed container 21 is capable of flowing freely through transfer conduit 60 into vessel 25 whenever the monomer is desired for being added into vessel 25. By providing a separate gas flow pathway (preferably ambient air) through gas-flow aperture 74 and gas-flow conduit 61, gas, such as nitrogen, argon, or other inert gas or air is constantly replaced in sealed container 21 as the monomer is withdrawn therefrom. In this way, the creation of a partial vacuum is avoided and free flow of the monomer is provided.

In the preferred construction, this embodiment of the present invention is completed by incorporating cover 70 that is constructed for being mounted in collar portion 55 for preventing and blocking any unwanted entry into collar portion 55, prior to the insertion of sealed container 21. In this way, contact with the terminating ends of piercing elements 63 and 66 is prevented and any unwanted or accidental injury is avoided.

In the preferred construction, cover 70 comprises an outwardly extending rim 71 formed on the base thereof, which cooperates with inwardly extending tabs 58, in order to secure cover 70 in the desired position. In addition, whenever monomer bearing sealed container 21 is ready for insertion in collar portion 55, cover 70 is easily removed from its secured position, thereby enabling sealed container 21 to be telescopically inserted and locked in position in collar portion 55.

6.1.1 Mixing and Dispensing Unit of the Invention

FIGS. 12–18 and the corresponding text below provide a detailed disclosure of the construction and operation of further embodiments of an apparatus for mixing and dispensing components termed a mixing and dispensing unit.

In operation, the mixing and dispensing unit of the invention 200 corresponds to bone cement handling and delivery system 22 of FIGS. 1–11 and as discussed in detail above. Transfer of liquid monomer under vacuum to mixing and dispensing unit of the invention 200 is substantially similar to the transfer procedure described above for vessel 25. Thus, the mixing and dispensing unit of the invention is preferably used in conjunction with sealed container 21 and fluid transfer assembly 23, (both of FIGS. 1, 2, 6, and 7).

Figure 12:
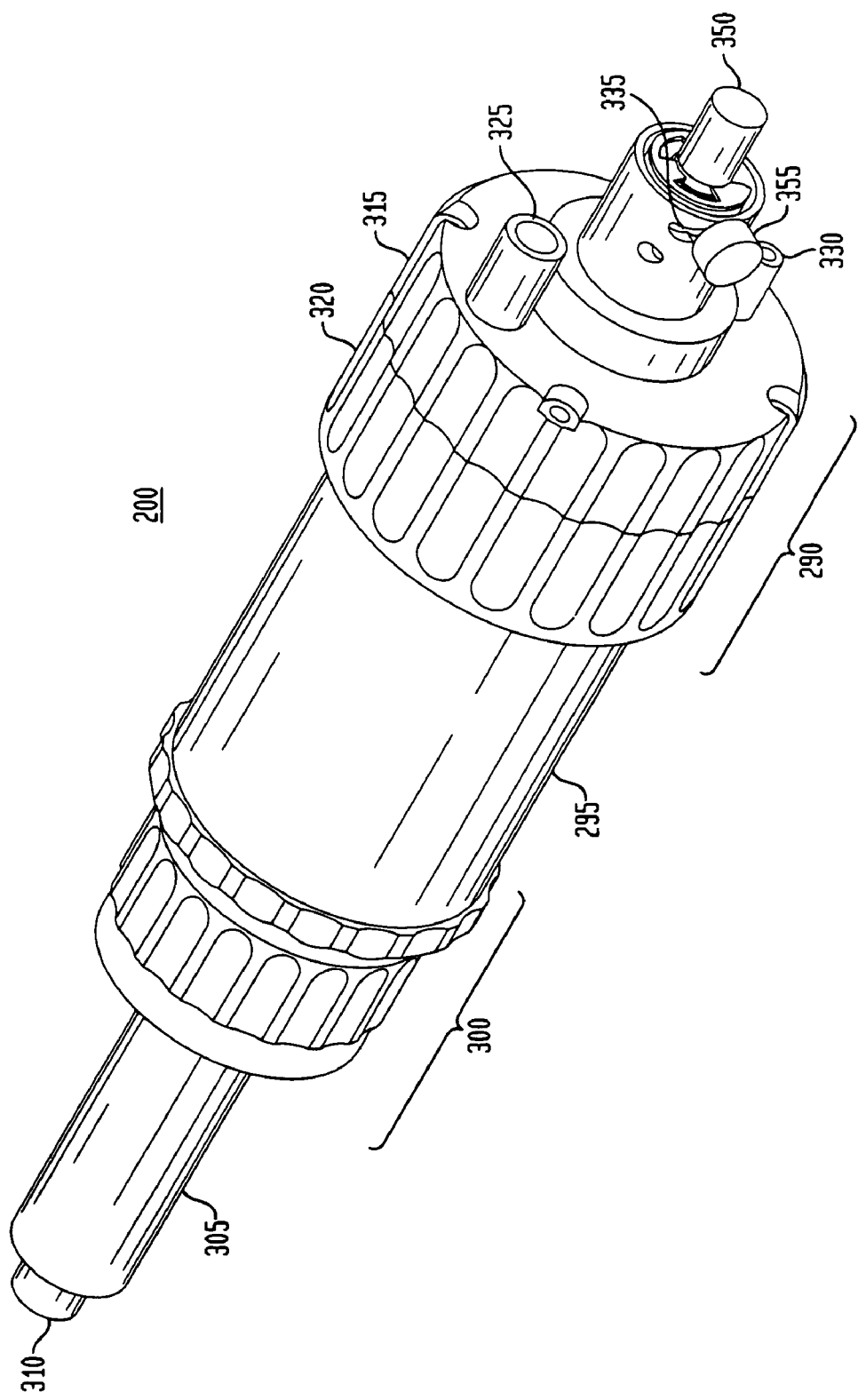
FIG. 12 is a perspective view of a fully assembled mixing and dispensing unit of the invention.

FIG. 12 depicts one embodiment of a fully assembled mixing and dispensing unit of the invention 200. Apparatus 200 comprises mixing chamber 295, controllable portal assembly 300, and dispensing chamber 305, preferably, tube shaped, having dispensing portal 310. Preferably, dispensing portal 310 is adapted to connect to the standard needle or cannula used in vertebroplasty procedures. Controllable portal assembly 300 comprises a controllable portal discussed in more detail below, which provides controlled opening of a flow path between the sealed mixing chamber 295 and dispensing chamber 305. In a preferred embodiment, mixing chamber 295 comprises cover assembly 290. Preferably, cover assembly 290 comprises top cap 315 attached to mixing-chamber cover 320 by way of set screws. Mixing chamber 295 comprises access portal 325, vacuum portal 330, and preferably comprises engagement-pin-slot 335 for receiving engagement pin 355.

Figure 13:
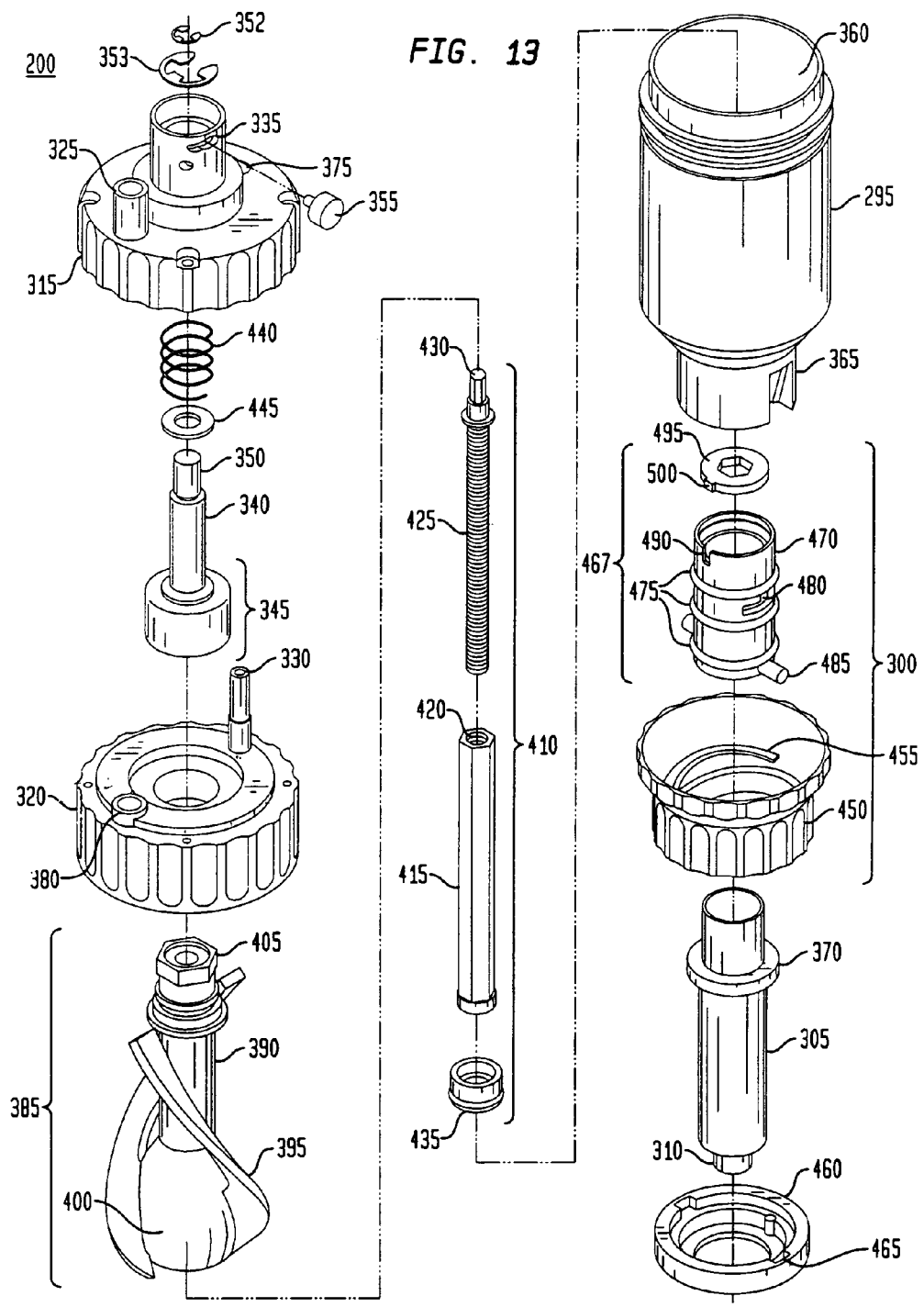
FIGS. 13 and 14 are exploded and cross-section side elevation views of a mixing and dispensing unit of the invention depicting the interrelation of component parts.
Figure 14:
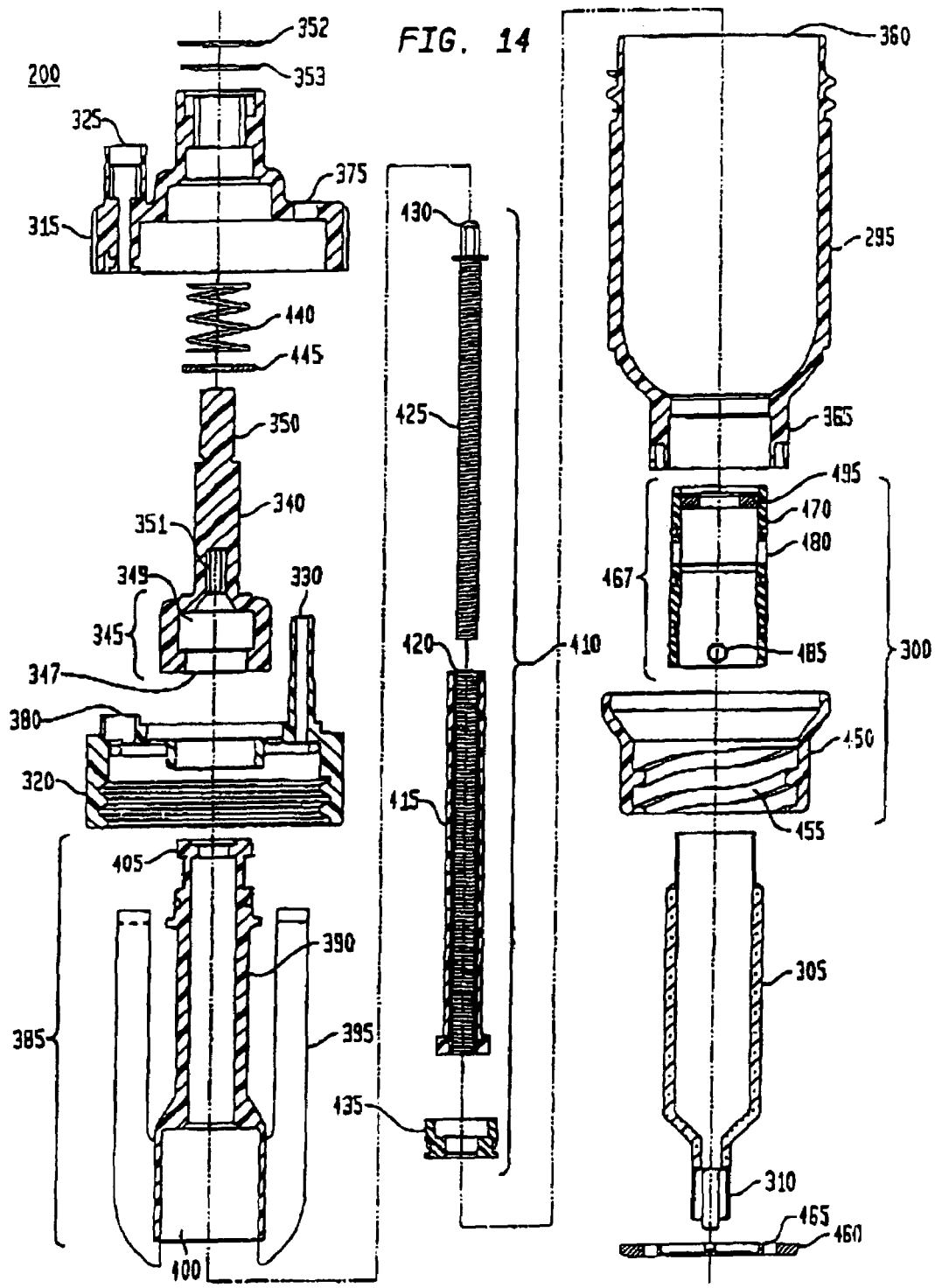

FIGS. 13 and 14 are exploded and cross-section side elevation views of apparatus 200 depicting the interrelation of component parts in a preferred embodiment of the mixing and dispensing unit of the invention. As illustrated in FIG. 13, mixing chamber 295 defines mixing cavity 360 for receiving the separate components to be mixed and dispensed. Preferably, mixing chamber 295 comprises a smaller-diameter end 365 to receive controllable portal assembly 300. Dispensing chamber 305 is connected to mixing chamber 295. When the controllable portal housed in controllable portal assembly 300 is closed, sealed mixing chamber 295 is isolated from dispensing chamber 305. On the other hand, opening the controllable portal creates a flow path so that dispensing chamber 305 can receive mixed components from mixing chamber 295 for dispensation. Preferably, dispensing chamber 305 comprises support flange 370.

As discussed above, in a preferred construction, mixing chamber 295 comprises cover assembly 290 (see FIG. 12), which, in turn, comprises end cap 315 and a mixing-chamber cover 320. In this embodiment, as shown in FIG. 13, end cap 315 comprises opening 375 aligned with vacuum portal 330, and mixing-chamber cover 320 comprises opening 380 aligned with access portal 325.

In a preferred embodiment of cover assembly 290, mixing chamber cover 320 attaches to mixing chamber 295 by threaded engagement. Mixing chamber 295 houses mixing-unit 385. Mixing unit 385 can be any assembly well known in the art to mix components, for example, but not limited to, mixers comprising mixing vanes, such as paddles, blades, and propellers. Preferably, mixing unit 385 comprises cylindrical, hollow mixing shaft 390 and helical mixing vanes 395. In a more preferred embodiment, hollow mixing shaft 390 comprises a large-diameter end 400 and mixing head 405.

The mixing and dispensing unit of the invention further comprises a drive mechanism to drive the mixed components from dispensing chamber 305 into the desired location. The drive mechanism can be any device well known in the art to drive contents from a chamber. Preferably, the drive mechanism comprises a plunger that can be driven by a rotational drive or simply by pushing the plunger down by hand.

The preferred drive mechanism 410 is shown in FIG. 13, which comprises plunger shaft 415 having bore 420, which houses axially-movable plunger shaft advancing member 425. Preferably, plunger advancing member 425 terminates in drive head 430 constructed for rotational engagement with drive-head engagement 351. Preferably, advancing-member 425 comprises male threads, and bore 420 comprises complimentary female threads. Preferably, plunger shaft 415 comprises plunger-sealing-end 435. Preferably, plunger-sealing-end 435 is constructed of a flexible, chemically resistant material and has a diameter slightly greater than the inner diameter of dispensing chamber 305 to ensure that all of the material contained within dispensing chamber 305 is axially advanced upon movement of plunger shaft 415. Preferably, drive mechanism 410 is housed by hollow mixing shaft 390.

Rotational drive 112 (shown in FIGS. 15–18 as an arrow indicating rotational movement) connects to rotating-means connection 350 of drop shaft 340. Rotating-means connection 350 is firmly secured to end cap 315 by lock washers 352 and 353. Rotational drive 112 can be any motorized or manually driven rotating device inducing rotation, which are well known in the art, for example, but not limited to a drill, handle, or hand crank. In the mixing stage, rotational drive 112 rotates mixing unit 385 by way of drop shaft 340. This is because, in the mixing stage, the lower portion 347 (see FIG. 14) of mixing unit connection 345 is engaged with mixing head 405. Mixing unit connection 345 comprises a lower portion 347 (see FIG. 14) having an interior configuration that is geometrically complementary to mixing head 405 (e.g., hexagonal) so as to rotationally engage the mixing head 405 (e.g., a hexagonal shape) and an upper portion 349 (see FIG. 14) having an interior configuration that will not engage mixing head 405 (e.g., a smooth round shape). Mixing unit connection 345 is designed in this manner so that when drop-shaft 340 is in the up position (mixing phase), mixing head 405 and drop-shaft 340 are rotationally engaged by way of complementary geometries between the lower portion 347 of mixing unit connection 345 and mixing head 405. On the other hand, after mixing is complete and the mixing chamber contents have been transferred to dispensing chamber 305, drop-shaft 340 is dropped, whereby the smooth round upper portion 349 (FIG. 14) of mixing unit connection 345 is adjacent to mixing head 405 and, in effect, drop-shaft 340 is disengaged from mixing head 405. Thus, rotation of drop-shaft 340 does not rotate mixing unit 385. This dispensing phase is explained in more detail below.

Figure 16:
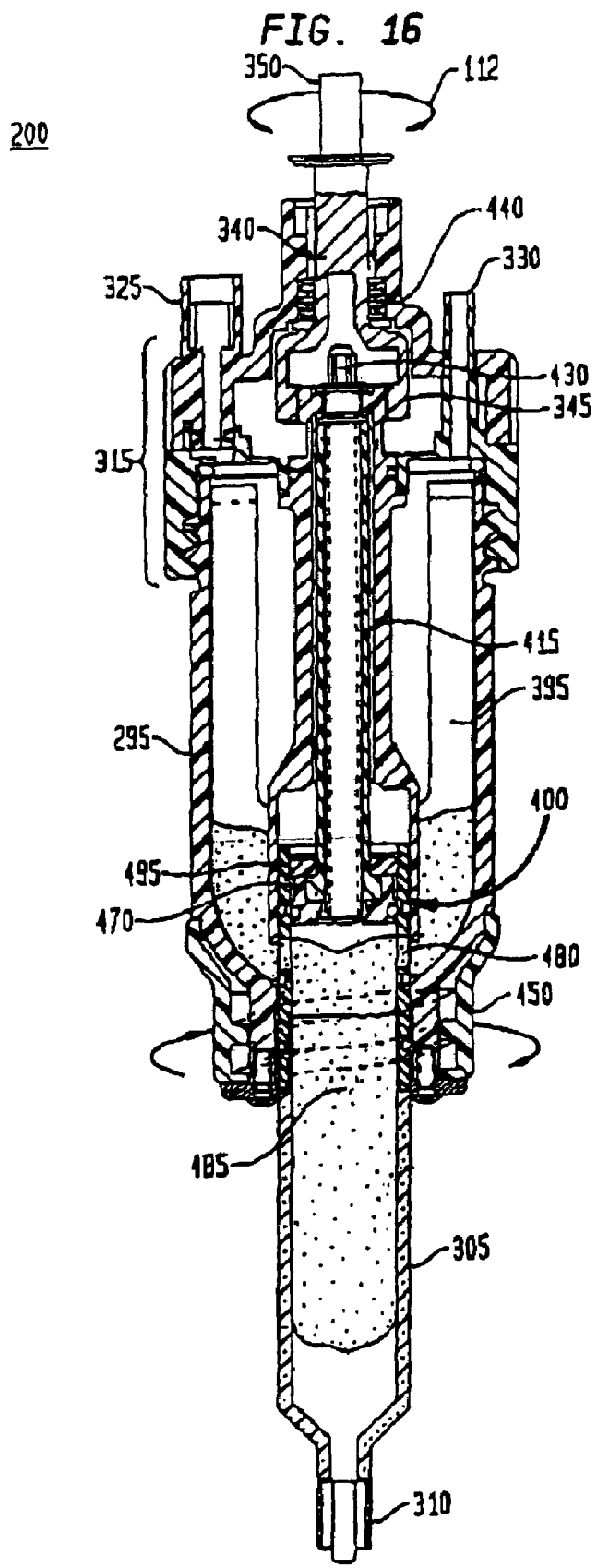
FIG. 16 is a cross-sectional view of a mixing and dispensing unit of the invention depicting the mixed components transferring to the dispensing chamber.

During the mixing stage, drop shaft 340 is in the up position such that drive-head engagement 351 is held above and is therefore not engaged with drive head 430. This is illustrated by FIGS. 15 and 16. At the point when dispensation is desired, however, by a simple mechanical adjustment (i.e., disengaging engagement pin 355), drop shaft 340 is forced down by the action of spring 440 and washer 445 with the result that the lower portion 347 (FIG. 14) of mixing unit connection 345 disengages from mixing head 405 and, at the same time, drive-head engagement 351 of drop shaft 340 engages with drive mechanism 410 by way of drive head 430. Then activation of rotational drive 112 controllably advances plunger 415. This aspect of the embodiment is illustrated by FIGS. 17 and 18.

As mentioned above, controllable portal assembly 300 comprises a mechanism for opening a flow path between mixing chamber 295 and dispensing chamber 305 after mixing of the components contained in mixing chamber 295 is complete. Such a mechanism is herein termed a controllable portal. FIG. 13 depicts a preferred controllable portal assembly 300 comprising locking collar 450, having threads 455, and end cap 460 having locking slots 465. Controllable portal assembly 300 connects to the base of mixing chamber 295. The controllable portal can be any valve, stopcock, or other device effective to isolate the contents of mixing chamber 295 from dispensing chamber 305 during the mixing phase and also to create a flow path between mixing chamber 295 and dispensing chamber 305 when transfer between mixing chamber 295 and dispensing chamber 305 is desired. A preferred embodiment of a controllable portal is depicted in FIG. 13 as 467.

Controllable portal 467 comprises sliding tube 470 securely fixed to dispensing chamber 305. Preferably, sliding tube 470 forms a tight seal with both the mixing chamber 295 and dispensing chamber 305, for example, by use of o-rings 475. In FIG. 13, sliding tube 470 comprises a pair of windows 480 on each side and radially extending locking rods 485. Sliding tube 470 further comprises plunger-locking-slot 490. Sliding tube 470 can be an integral part of dispensing chamber 305 or can be a separate component for secure, fixed attachment to dispensing chamber 305. In a preferred embodiment, radially extending locking rods 485 are positioned for cooperating, controlled, sliding engagement with threads 455 of locking collar 450. Guide washer 495 is designed to be geometrically complementary to plunger shaft 415 so as allow plunger shaft 415 to move up and down along its axis but not to rotate. Guide washer 495 comprises tooth 500 complementary in shape to plunger-locking-slot 490.

6.1.1.1 The Mixing Phase of the Mixing and Dispensing Unit of the Invention

The components to be mixed are contained within mixing chamber 295. One or more of the components can be prepackaged in the mixing and dispensing unit and/or additional components can be added directly before mixing.

As shown in FIG. 15, during the mixing phase, sliding tube 470 is positioned by threads 455 of locking collar 450 so that: (1) windows 480 are within large-diameter end 400 of hollow mixing shaft 390; and (2) the flow path (i.e., windows 480) between mixing chamber 295 and dispensing chamber 305 is blocked. In other words, the interior of dispensing chamber 305 is isolated from the interior of mixing chamber 295, preventing the contents from entering dispensing chamber 305 during mixing.

Further, in this mixing phase, drop shaft 340 is engaged by engagement pin 355 and therefore locked in the up position such that drive head 430 is not engaged with rotating-drive-head engagement 351. And in the up position, as discussed above, drop shaft 340 is rotationally engaged with mixing head 405. Also, advancing member 425 is fully inserted into bore 420. Tooth 500 of guide washer 495 is engaged with locking-slot 490 so that plunger shaft 415 is prevented from rotating.

In the above configuration, upon connection and operation of a rotational drive 112 to rotating-means connection 350, mixing unit 385 is rotated along its axis thereby mixing the components within mixing chamber 295.

6.1.1.2 Transfer of Mixed Components from Mixing Chamber to Dispensing Chamber of the Mixing and Dispensing Unit of the Invention When the mixing phase is complete, the contents of mixing chamber 295 are ready for transfer to dispensing chamber 305. This is accomplished by opening controllable portal 467 to create a flow path. In a preferred embodiment, rotation of helical shaped mixing vanes 395 is used force the contents of mixing chamber 295 into dispensing chamber 305 by action of mixing unit 385.

FIGS. 15 and 16 illustrate operation of controllable portal 467 to open a flow path between mixing chamber 295 and dispensing chamber 305 and using the action of mixing unit 385 to transfer the contents. First locking collar 450 is rotated whereupon locking rods 485 are guided within threads 455 of locking collar 450 thereby pushing sliding tube 470 and dispensing chamber 305 downward such that windows 480 are below plunger-sealing-end 435 and a flow path between mixing chamber 295 and dispensing chamber 305 is created. Thus, the axial rotational movement of locking collar 450 causes windows 480 of sliding tube 470 to move out of engagement with the larger diameter end 400 of hollow mixing shaft 390, whereby windows 480 are positioned below plunger-sealing-end 435 to complete the flow path.

Rotating of locking collar 450 is complete when locking rods 485 are locked within complementary locking slots 465 of end cap 460. The construction of locking rods 485 and locking collar 450 effectively provide a turnbuckle construction that causes dispensing chamber 305 to move downward.

Once dispensing chamber 305 is in the position depicted in FIG. 16, rotational drive 112 is activated to force the contents of mixing chamber 295 into dispensing chamber 305 by the helical action of mixing unit 385.

6.1.1.3 The Dispensing Phase of the Mixing and Dispensing Unit of the Invention Once the contents are loaded into dispensing chamber 305, drop shaft 340 can be dropped by releasing engagement pin 355. This causes drive-head engagement 351 of drop shaft 340 to rotationally engage with drive head 430 of plunger advancing member 425. At the same time the upper portion 349 (FIG. 14) of mixing unit connection 345, having a smooth interior (not shown), drops over mixing head 405 and the geometrically complementary lower portion 347 (FIG. 14) of connection 345 disengages from mixing head 405. Accordingly, in this position, the rotation of drop-shaft 340 does not rotate mixing unit 385. Dispensing the contents of dispensing chamber 305 is illustrated in FIGS. 17 and 18.

Upon activating rotational drive 112, rotating means connection 350 is controllably rotated. The rotational movement causes plunger advancing member 425 to rotate. Since plunger advancing member 425 is axially fixed (cannot move up and down but can only rotate), plunger shaft 415 and plunger-sealing-end 435 are controllably axially advanced longitudinally through dispensing chamber 305. The longitudinal movement of plunger-sealing-end 435 in dispensing chamber 305 forces the mixed components contained therein to be delivered through outlet portal 310 of dispensing chamber 305. Preferably, dispensing portal 310 is adapted to connect to the standard needle or cannula (not shown) used in vertebroplasty procedures.

In addition, by controlling the rotational movement or speed of rotating-means connection 350, the precisely desired pressure for advancing the mixed components through dispensing chamber 305 is achieved. Furthermore, by stopping the rotational movement of rotating-means connection 350 or reversing the direction rotating-means connection 350, complete control over the delivery of the mixed components to the precisely desired site is achieved. In fact, by reversing the rotation of rotating-means connection 350, the plunger direction is reversed and the contents can actually be pulled back into dispensing chamber 305. This provides much greater control than previously available. In addition, in the preferred embodiment, reference indicia are marked or etched on the outer surface of dispensing chamber 305, thereby enabling the operator to precisely measure the quantity of material being delivered.

In another convenient embodiment, the mixing and dispensing unit of the invention can be calibrated such that the number of revolutions of drop shaft 340 and/or the rotational drive 112 corresponds to an amount (e.g., a weight or volume) of bone cement dispensed. In this embodiment, a clinician dispensing a biocompatible filler using the mixing and dispensing unit of the invention can dispense a predetermined amount by completing a pre-determined number of rotations of drop shaft 340 and/or rotational drive 112.

In view of the above disclosure, it is clear that in one embodiment, the invention is directed to an apparatus for mixing and dispensing components comprising:

(a) a sealed mixing chamber having an access portal and a vacuum portal;

(b) a dispensing chamber connected to the sealed mixing chamber, wherein the dispensing chamber is isolated from the mixing chamber;

(c) a controllable portal for opening a flow path between the sealed mixing chamber and the dispensing chamber after the components are mixed;

(d) a drive mechanism associated with the dispensing chamber for driving the mixture from the dispensing chamber.

Preferably, the apparatus further comprises:

a. a sealed container for containing a first component; and b. a transfer assembly for providing a flow path between the sealed container and the sealed mixing chamber, wherein, in operation, when the sealed container comprises the first component, connection of vacuum to the vacuum portal induces the first component to transfer into the sealed mixing chamber by way of the flow path.

In another embodiment, the invention is directed to a method for mixing and dispensing components comprising:

(a) adding the components to an apparatus comprising:
 (i) a sealed mixing chamber comprising an access portal and a vacuum portal,
 (ii) a dispensing chamber connected to the sealed mixing chamber, wherein the dispensing chamber is isolated from the mixing chamber,
 (iii) a controllable portal,
 (iv) a drive mechanism associated with the dispensing chamber;

(b) mixing the components in the mixing chamber to form a mixture;

(c) opening the controllable portal to create a flow path between the sealed mixing chamber and the dispensing chamber;

(d) transferring the mixture to the dispensing chamber by way of the flow path; and (e) activating the drive mechanism to dispense the mixture from the dispensing chamber.

6.1.1.4 Illustrative Embodiment—Manually Actuable Mixer and Dispenser

Aspects of the invention may now be more clearly understood by consideration of the following specific embodiment in the form of a manually actuable mixing and dispensing apparatus. By manually actuable is meant that both mixing of the components and dispensing of the mixed components can be manually effected and controlled without the use of power tools. One advantage of manual actuation is that operation is not dependent on the presence of power tools or electrical outlets in a sterile environment. Another is the finer level of control provided by direct hand control.

Figure 19A:
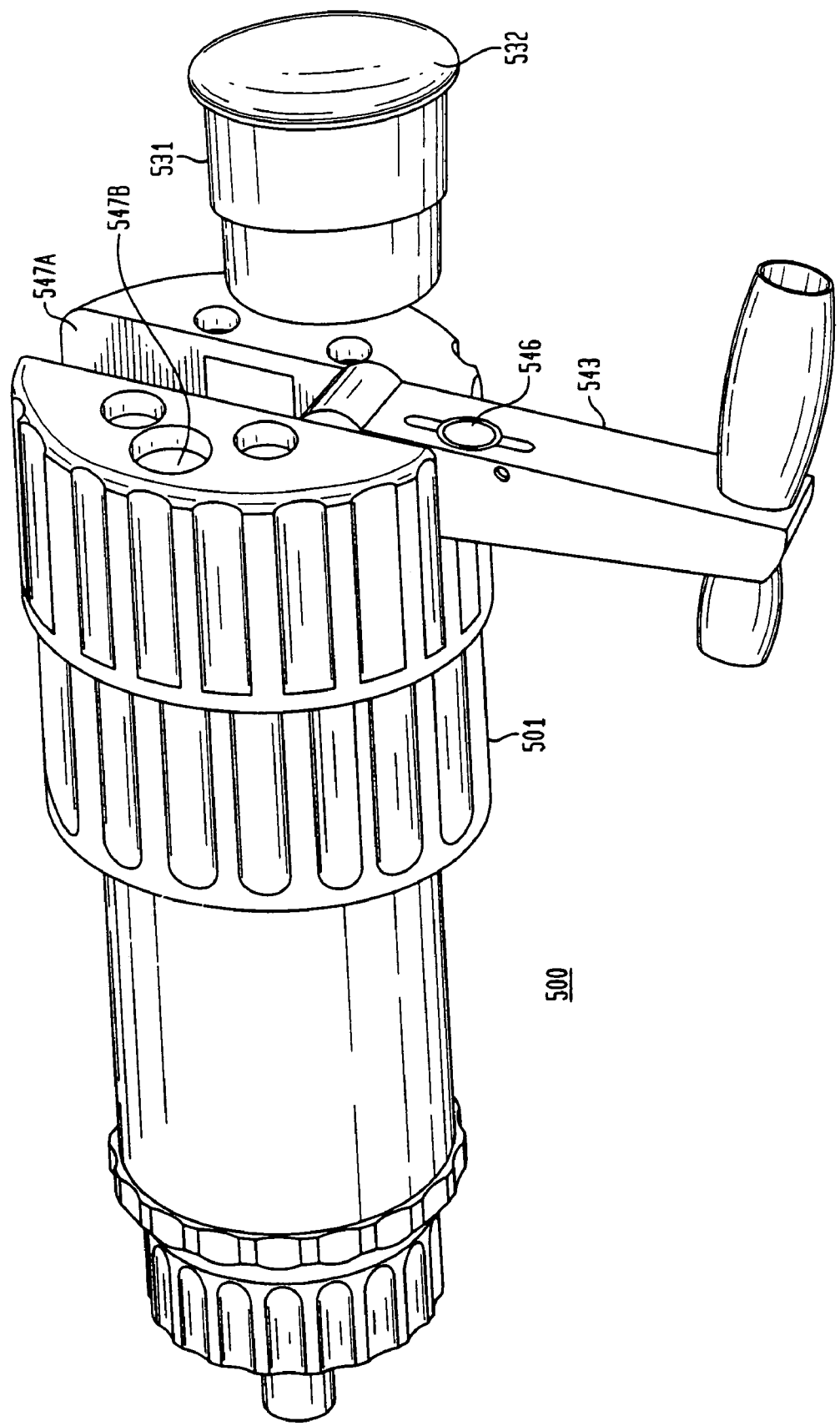
FIGS. 19A and 19B are perspective views of an exemplary manually actuable apparatus in condition for mixing and dispensing, respectively.
Figure 19B:
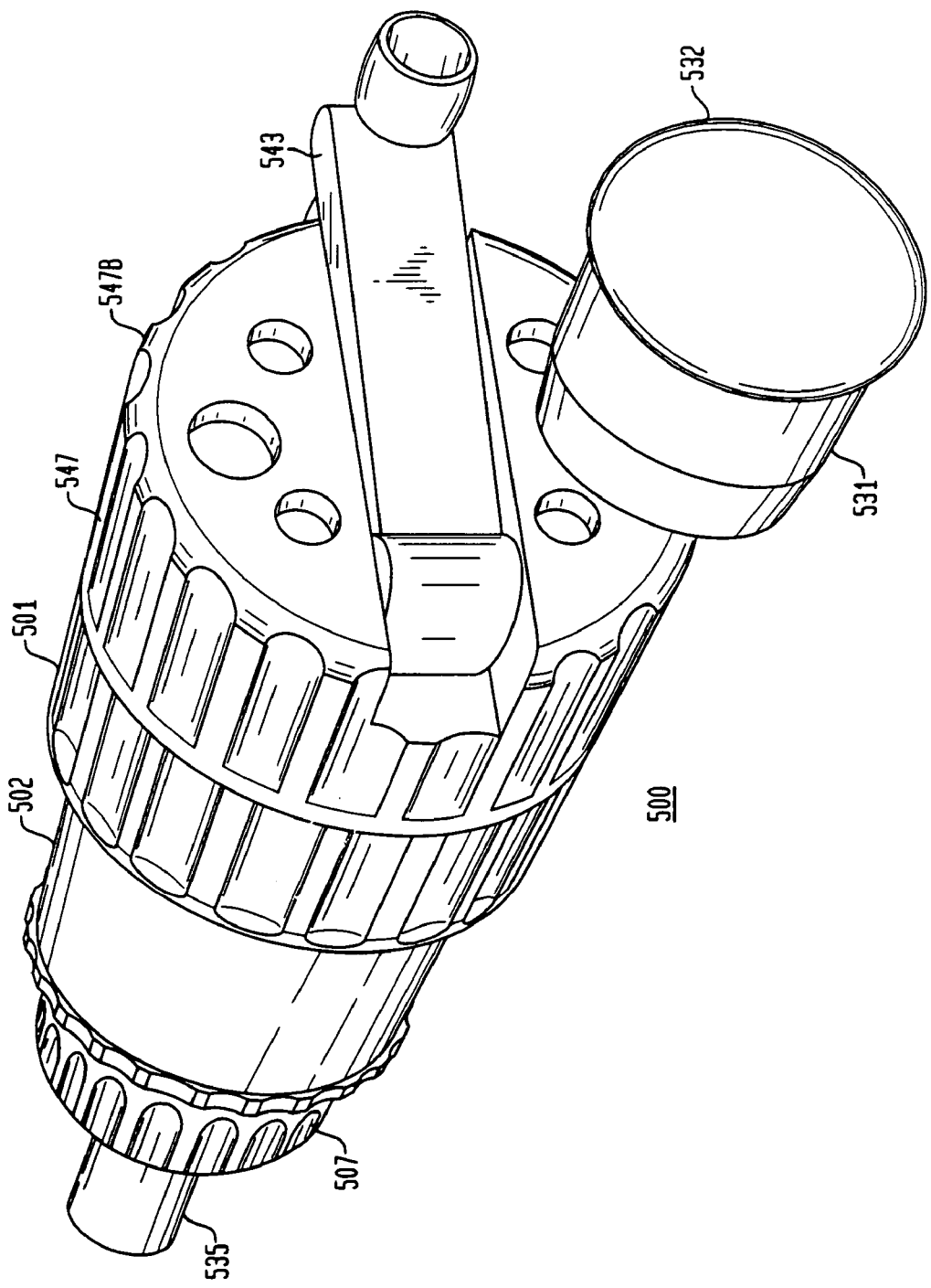

The exemplary apparatus is similar in structure and function to the apparatus previously illustrated and described except that it provides adaptions to facilitate manual mixing and manual dispensing of the mixed components. FIG. 19A is a perspective view of the assembled exemplary apparatus 500 with a radially extending handle 543 in a first position to facilitate manual mixing of liquid monomer and bone cement powder. The handle 543 is pivotally mounted on a handle cap 547. FIG. 19B shows the same apparatus 500 with the handle 543 pivoted to a second position to facilitate dispensing the mixture. The assembled apparatus 500 comprises a mixing chamber 502, controllable portal assembly 507, and dispensing chamber 535, preferably tube shaped, having a dispensing portal (not visible). Preferably the dispensing portal is adapted to connect to the standard needle or cannula used in vertebroplasty procedures. The controllable portal assembly 507 provides controlled opening of a flowpath between the sealed mixing chamber 502 and dispensing chamber 535. Preferably mixing chamber 502 comprises a top cap 501.

Figure 20:
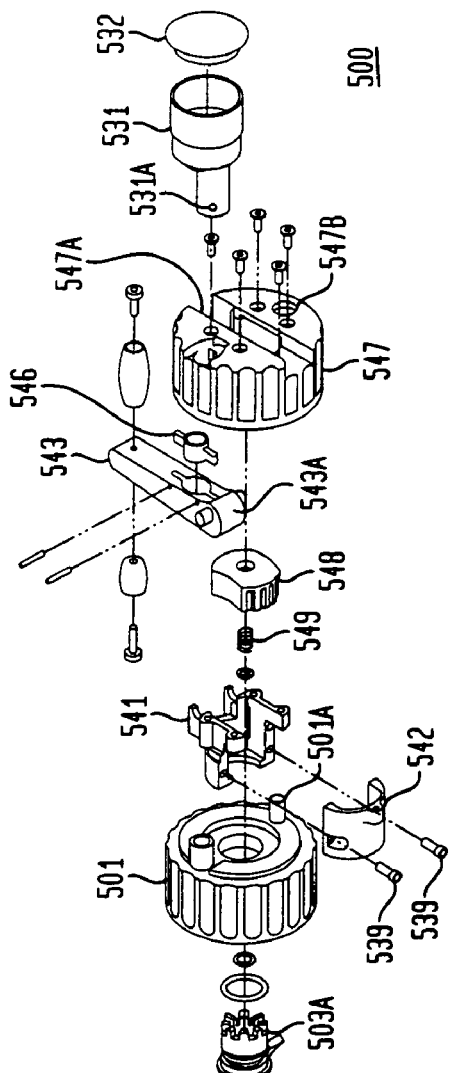
FIG. 20 is an exploded view of the exemplary manually actuable apparatus.

FIG. 20 is an exploded view of the exemplary manually actuable mixing and dispensing apparatus 500. The apparatus is similar in operation and structure to those already described herein. The discussion here will emphasize the modifications found advantageous for manual actuation.

It is contemplated that the apparatus 500 will be delivered with the crank handle 543 in the open radially extended position (FIG. 19A) and the needle transfer housing 531, 532 in place. The user will remove the cover 532 of the needle transfer housing 531 and attach a vacuum source (not shown) to the vacuum port 501A as previously described. With vacuum applied, needles of the transfer housing pierce the cap of a monomer vial and liquid monomer from the vial is drawn into the transfer housing 531.

The monomer is further drawn into the mixing housing 502 which can contain the powder polymer. The vial and the transfer housing 531 are then removed together, the simultaneous removal assured by locking fingers of the transfer housing locking onto the cap of the vial.

The user then mixes the monomer and powder to form bone cement by rotating the radially extended handle 543 or by rotating the handle cap 547 (which acts as a knob). With the handle 543 in open position, a cam surface 543A pushes downward on a crank handle gear 548 causing the gear configuration to interface with a corresponding gear configuration 503A on the end of mixing paddle 503. The manual rotational movement of the handle or knob is thus transmitted to actuate the mixing paddle 503.

When the cement is mixed, the user rotates the controllable portal assembly 507 to open the controllable port between the mixing chamber 502 and the dispensing syringe tube 535. The handle 543 is then turned to move the mixed material through the now open port into the syringe tube 535.

After the syringe tube 535 is filled, the user flips the hinged handle 543 across the center of the cap 547 to lock the handle in the second position (FIG. 19B) into a receiving slot 547A of the cap. This change of handle position releases the pressure of the crank handle cam 543 on the crank handle gear 548, permitting the spring biased gear to move upward, disengaging the gear from the paddle 503. In the second position, a hex cap 546 in the handle 543 engages the drive configuration 511A of a threaded plunger shaft 511. The paddle is thus disengaged so that it does not move or mix during the discharge of material from the apparatus, and the handle is engaged with threaded shaft 511 for driving the mixed material out through syringe tube 535.

The user then rotates handle 543 or the knobbed crank handle cap 547 to actuate the plunger mechanism (511, 518, 533) pushing the mixed material out the end of the syringe tube 535 and typically into a needle or cannula (not shown).

Component Structure

The needle housing 531 and needle housing cap 532 are preferably of the design shown and described in connection with FIG. 9. Advantageously the needle housing 531 has a detent bump 531A in the lower tube portion to hold the housing in place during shipment and preparation. The needle housing in place also aligns the vacuum port 501A with an opening 547B in the crank handle cap 547 to facilitate the attachment of a vacuum line (not shown). Alternatively, the vacuum port 501A can be disposed on the exterior of the mixing chamber or the end cap to facilitate attachment. Crank handle cap 547 houses the crank handle 543 and assembled knob components.

The crank handle is held in place by a crank handle cup comprising a pivot half 541 and a clamp half 542, each secured to the crank handle cap 547. The cup (541, 542) also houses the crank handle gear 548, permitting it to slide longitudinally. The longitudinal position of the gear 548 is controlled by the cam surface 543A of the handle. The gear is loaded by spring 549 in the disengaged condition with respect to the mixing paddle 503. Thus when the handle is in the first position (FIG. 19A), the gear is engaged with the paddle. Pivoting the handle to the second position (FIG. 19B) releases the gear to its spring biased disengaged position.

The crank handle cup assembly (541, 542) also locks onto the top end of the paddle 503 to provide alignment between the paddle and the gear 548. The two halves 541, 542 are secured together as by screws 539 or snap-fit connections (not shown). The cup could also be molded as a one piece part.

The end cap 501 is advantageously similar to top cap 315 of FIG. 12. It attaches the upper cap assembly to the mixing chamber 502.

The mixing paddle 503 is advantageously similar to paddle 390 of FIG. 13, except that the drive end 503A has a gear configuration for interfacing with the crank handle gear 548. It is preferred that the top of the drive end 503A have lead-in edges to assist in engagement with the crank handle gear.

In other regards, the drive mechanisms for mixing and dispensing and the mechanisms for operating the controllable port between the mixing chamber and the dispensing chamber are the same as those described for other embodiments herein.

It can now be seen that the exemplary apparatus for manually mixing and dispensing components comprises a sealed mixing chamber having an access portal and a vacuum portal, a mixing unit in the mixing chamber to mix the components, and a first manually actuable drive mechanism associated with the mixing unit to actuate mixing.

The apparatus further includes a dispensing chamber connected to the sealed mixing chamber but which is isolated from the mixing chamber. A controllable portal is provided for opening a flow path between the sealed mixing chamber and the dispensing chamber after the components are mixed. A second manually actuable drive mechanism associated with the dispensing chamber is provided to drive the mixture from the dispensing chamber.

In advantageous forms, the mixing chamber is preloaded with bone cement powder. The first and second drive mechanisms comprise rotationally movable handles or knobs and preferably a common handle or knob. A mechanical switching arrangement can be provided to disengage the common handle or knob from the first drive mechanism. The preferred mixing unit comprises a mixing paddle, and the preferred second drive mechanism comprises a plunger shaft.

Although the present invention has been described in considerable detail with reference to certain preferred embodiments and versions, other versions and embodiments are readily implemented by those of skill in the art. Therefore, the scope of the appended claims should not be limited to the description of the versions and embodiments expressly disclosed herein.

It is understood that the above-described embodiments are illustrative of only a few of the many possible specific embodiments, which can represent applications of the invention. Numerous and varied other arrangements can be made by those skilled in the art without departing from the spirit and scope of the invention.

What is claimed is:

1. An apparatus for manually mixing and dispensing components comprising:
    a sealed mixing chamber having an access portal and a vacuum portal;
    a mixing unit in the mixing chamber to mix the components;
    a dispensing chamber connected to the sealed mixing chamber, wherein the dispensing chamber is isolated from the mixing chamber;
    a controllable portal for opening a flow path between the sealed mixing chamber and the dispensing chamber after the components are mixed;
    a dispensing mechanism in the dispensing chamber adapted to expel material from the dispensing chamber; and
    a manually actuable crank handle, that is movable to a first position to engage the mixing unit and disengage the dispensing mechanism, movable to a second position to engage the dispensing mechanism and disengage the mixing unit, and movable to drive the engaged mixing unit or the engaged dispensing mechanism.

2. An apparatus for manually mixing and dispensing components comprising:
    a mixing chamber having an access portal;
    a mixing unit in the mixing chamber;
    a dispensing chamber connected to the mixing chamber;
    a dispensing mechanism in the dispensing chamber adapted to expel material from the dispensing chamber;
    a controllable portal for opening a flow path between the mixing chamber and the dispensing chamber after the components are mixed; and
    a crank handle that is movable to a first position to engage the mixing unit and disengage the dispensing mechanism, movable to a second position to engage the dispensing mechanism and disengage the mixing unit, and movable to drive the engaged mixing unit or the engaged dispensing mechanism.

3. The apparatus of claim 2 wherein the mixing chamber contains bone cement powder.

4. The apparatus of claim 2 wherein the crank handle is rotationally movable.

5. The apparatus of claim 2 wherein the mixing unit comprises a mixing paddle.

6. The apparatus of claim 2 wherein the dispensing mechanism comprises a plunger shaft.

7. The apparatus of claim 2 wherein the mixing chamber comprises a powder component to be mixed with a liquid component and further comprising a transfer housing to facilitate transfer of the liquid component into the mixing chamber.

8. The apparatus of claim 2 wherein the crank handle is adapted to pivot about a hinge between the first position and the second position.

9. The apparatus of claim 2 wherein the crank handle is adapted to rotate about an axis to drive the engaged mixing unit or the engaged dispensing mechanism.

10. The apparatus of claim 2 further comprising a handle cap coupled to the mixing chamber and rotatable about an axis relative to the mixing chamber and the dispensing chamber, wherein the crank handle is coupled to the handle cap with a hinge connection and wherein rotation of the crank handle also rotates the handle cap.

11. A method comprising:
    introducing mixable components into a mixing chamber of a component mixing and dispensing apparatus, the mixing chamber having a mixing unit therein;
    moving a crank handle coupled to the mixing chamber to a first position to engage the mixing unit and disengage a dispensing mechanism in a dispensing chamber of the apparatus;
    with the crank handle in the first position, moving the crank handle to drive the mixing unit;
    manipulating a controllable portal coupled to the mixing chamber to allow the mixable components to flow from the mixing chamber into the dispensing chamber;
    moving the crank handle to a second position to engage the dispensing mechanism that is adapted to drive the mixable components from the dispensing chamber and to disengage the mixing unit;
    with the crank handle in the second position, moving the crank handle to actuate the dispensing mechanism.

12. The method of claim 11 wherein moving the crank handle between the first position and the second position comprises pivoting the crank handle on a hinge.

13. The method of claim 11 wherein moving the crank handle to drive the mixing unit comprises rotating the crank handle about an axis; and
    wherein moving the crank handle to actuate the dispensing mechanism comprises rotating the crank handle about the axis.

* * * * *